United States Patent [19]

Tachibana et al.

[11] Patent Number: 5,694,883
[45] Date of Patent: Dec. 9, 1997

[54] NEMATODA CULTIVATING METHOD

[75] Inventors: Mineo Tachibana; Toshihito Uechi; Nobukazu Suzuki; Tadaaki Kawasugi, all of Ryuugasaki, Japan

[73] Assignee: Kubota Corporation, Osaka, Japan

[21] Appl. No.: 403,879

[22] PCT Filed: Jul. 21, 1994

[86] PCT No.: PCT/JP94/01204

§ 371 Date: Jan. 29, 1996

§ 102(e) Date: Jan. 29, 1996

[87] PCT Pub. No.: WO95/02958

PCT Pub. Date: Feb. 2, 1995

[30] Foreign Application Priority Data

Jul. 23, 1993 [JP] Japan ............................ 5-182307

[51] Int. Cl.$^6$ ............................................. A01K 67/03
[52] U.S. Cl. ................................................. 119/6.7
[58] Field of Search ............................... 119/6.5, 6.7

[56] References Cited

U.S. PATENT DOCUMENTS 5,023,183  6/1991  Friedman et al. ................. 119/6.7

FOREIGN PATENT DOCUMENTS 6463326  9/1987  Japan .
1254607  4/1988  Japan .
06276892A  10/1994  Japan ............................. 119/6.5

Primary Examiner—John J. Wilson
Assistant Examiner—Yvonne R. Abbott
Attorney, Agent, or Firm—Felfe & Lynch

[57] ABSTRACT

The present invention relates to a method of cultivating, in medium, Steinernema kushidai (hereinafter simply called kushidai) which is one type of Nematoda. Kushidai has a strong insecticidal ability to kill larvae of coliopterous insects, and cultivation of large quantities of kushidai having the strong insecticidal ability requires conditions different from the techniques of cultivating other nematodes parasitic on insects.

Kushidai is cultivated in a medium including asteroid. This increases the insecticidal activity with respect to insects harmful to plants such as crops. The medium including asteroid may be adsorbed to a plurality of supports, and then the supports may be stacked with gaps thereamong to form a layer. This enables kushidai to be cultivated efficiently. Further, a liquid medium including asteroid may be prepared, with cultivation carried out while agitating the medium and supplying oxygen thereto. This obtains kushidai having a high multiplication characteristic and high insecticidal activity. The kushidai is used as a biological agrochemical to reduce damage done to crops such as sweet potato by harmful insects.

12 Claims, 1 Drawing Sheet

NEMATODA CULTIVATING METHOD

TECHNICAL FIELD

The present invention relates to a Nematoda cultivating method, and more particularly to a method of cultivating *Steinernema kushidai* (hereinafter simply called kushidai) in medium.

BACKGROUND ART

Nematodes parasitic on insects, in conditions of contact with host insects, enter the blood, body and cavities of the insects through the mouth, anus, spiracles and the like of the insects, and destroy the immune mechanism of the host insects by releasing symbiont bacteria kept in the body, thereby causing the death of the host insects. This characteristic is utilized in a known method for killing insects harmful to plants such as crops to prevent damage to the plants. Nematodes having such characteristic have heretofore been cultivated in large quantities also.

Incidentally, kushidai relating to the present invention is a relatively new type of Nematoda isolated in 1984 by Kushida et al. of the Forestry Experiment Station in Hamakita, Shizuoka Pref. Said kushidai has a strong insecticidal ability to kill larvae of coliopterous insects such as lamelicorn beetles. This is a peculiar property distinct from the strong insecticidal ability of known nematodes parasitic on insects, such as *Steinernema carpocapsae*, *Steinernema feltiae* and *Heterorhabditis bacteriphora*, to kill mainly lepidopterous insects. Thus, it has been suggested that kushidai has an insecticidal mechanism different from other nematodes. It is thought that conditions suited to its cultivation are different from the cultivating technique for other known nematodes parasitic on insects.

The present invention has been made on the finding of the fact that, when a medium containing asteroid is used in cultivating kushidai in medium, said kushidai exhibits a high degree of insecticidal activity. Its object is to provide a method of cultivating large quantities of kushidai having a high degree of insecticidal activity.

DISCLOSURE OF THE INVENTION

To fulfill this object, a first characterizing feature lies in cultivation of kushidai in a medium including asteroid.

Inventors have established, by experiment, the fact that, when cultivating known nematodes parasitic on insects, such as *Steinernema carpocapsae* strain ALL (hereinafter simply called ALL), cultivation in a medium including a steroid does not increase its insecticidal activity, but cultivation of kushidai in a medium including asteroid may significantly increase its insecticidal activity compared with cultivation in an ordinary medium not including asteroid. Thus, it has been found that, by including asteroid in a kushidai cultivating medium, the steroid specifically acts on kushidai to produce an insecticidal activity increasing effect not seen in other nematodes, and the kushidai cultivated in that medium exhibits a high degree of insecticidal activity.

That is, kushidai having a high insecticidal activity are now obtained by cultivating kushidai in a medium including asteroid.

A second characterizing feature lies in causing a medium (3) including a steroid to be adsorbed to a plurality of supports, then stacking the supports with gaps thereamong to form a layer, and cultivating *Steinernema kushidai* in said layer.

With such characterizing feature, said gaps allow a sufficient supply of oxygen for cultivating kushidai efficiently.

A third characterizing feature lies in preparing a liquid medium including a steroid, placing the liquid medium in a cultivating container in a condition to supply oxygen into said liquid medium and to agitate the same, and cultivating kushidai in said cultivating container.

With such characterizing feature, since the medium including asteroid is a liquid medium, cultivation may be carried out along with agitation and oxygen supply to cultivate kushidai efficiently.

Said medium including asteroid may be formed by preparing a solution of the steroid dissolved in heated oil and adding the solution to the medium. Said medium including asteroid may be formed by preparing a solution of the steroid dissolved in an organic solvent, adding oil to the solution, then preparing an emulsified suspension, and adding the suspension to the medium.

Consequently, the steroid may be dispersed uniformly in the medium to cultivate kushidai with high multiplication efficiency. Since the uniform dispersion in the medium is effected with facility, the steroid may easily be dispersed even in a liquid medium. Since a liquid medium, generally, provides a better efficiency of utilizing nutrients than a solid medium, kushidai may be cultivated with a further enhanced multiplication efficiency.

Preferably, said steroid is at least one of cholesterol and 4-cholesten-3-one.

This produces an effect of greatly increasing the insecticidal activity while maintaining a high multiplication characteristic of kushidai.

Thus, as described above, kushidai having a high insecticidal activity may be cultivated with a high multiplication characteristic. Moreover, said kushidai may be used as a biological agrochemical to kill insects harmful to crops such as sweet potato. Use of said kushidai as a biological agrochemical can significantly reduce damage done to said crops by harmful insects. It is now possible to provide large quantities of kushidai for the technique of utilizing Nematoda in helping to increase harvest of said crops.

Figure 1:
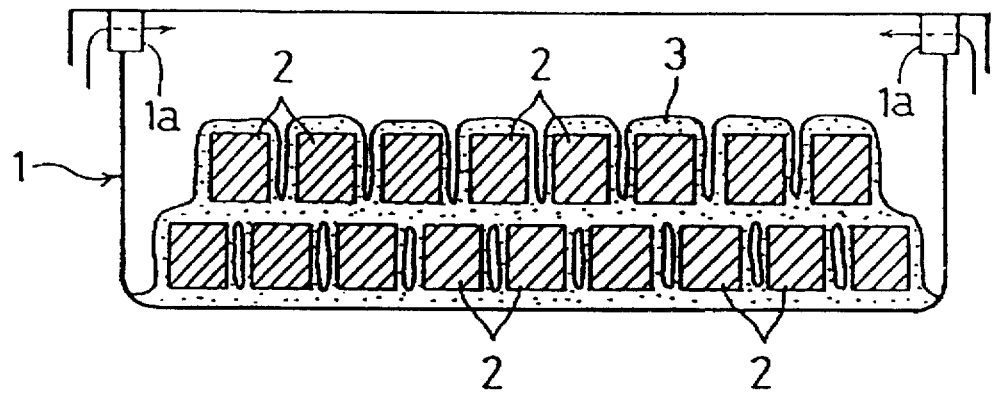
FIG. 1 is a schematic view showing a cultivating method in Test 4.

BEST MODE FOR CARRYING OUT THE INVENTION 2000 kushidai were inoculated into 20 ml agar medium prepared by adding 3% corn oil and 0.1% cholesterol to SGPY medium, and cultivated at 25° C. and at 70% relative humidity for 20 days. They were found to increase 235-fold. A bioassay was carried out using larvae in the third instar of *Anomala cuprea* Hope as sample insects. It was found that these kushidai had a greatly increased insecticidal activity compared with the kushidai cultivated in a medium not containing cholesterol (agar medium prepared by adding 3% corn oil to SGPY medium).

SGPY medium was prepared by adjusting an aqueous solution of 0.6% soluble starch
1.0% D-glucose
1.5% bactopeptone
1.5% yeast extract to pH 7.0 with sodium hydroxide and adding 0.3% agar. This medium was used after a usual sterilization process.

The bioassay is carried out as follows.

In the paper contact method, nematodes having multiplied are first extracted from the nematode culture by Baermann Funnel method and counted. A nematode suspension containing a predetermined quantity of nematodes and a plurality of vessels with filter paper placed in Petri dishes of 50 mm diameter are prepared. Next, said nematode suspension and one sample insect are placed and bred in each vessel. Its life or death is observed to determine insecticidal activity.

In the soil mixing method, a nematode suspension is first prepared as in the paper contact method. A plurality of plastic cups containing a mixture of 2 g sterilized leaf soil and 2 g distilled water are also prepared. Next, one sample insect and the nematode suspension are placed and bred in each plastic cup. Its life or death is observed.

Tests of kushidai cultivation carried out under varied conditions are shown hereinafter.

Test 1: Influence of Cholesterol Addition on the Insecticidal Activity of Kushidai How cholesterol plays a part in the multiplication characteristic and insecticidal activity of kushidai was examined.

(1) 2000 kushidai were cultivated, to examine its multiplication characteristic, in SGPY medium, in SGPY medium containing 3% corn oil (hereinafter abbreviated to SGPY—CO medium), in SGPY medium containing 3% rape seed oil (hereinafter abbreviated to SGPY—RO medium), in SGPY medium containing 3% linseed oil (hereinafter abbreviated to SGPY—LO medium), in SGPY medium containing 3% sesame oil (hereinafter abbreviated to SGPY—SO medium), and in SGPY medium containing 3% olive oil (hereinafter abbreviated to SGPY—OO medium). Further, they were cultivated for 20 days, to examine multiplication characteristic thereof, in SGPY medium to which 0.1% cholesterol was added (hereinafter abbreviated to SGPY—CS medium) and in SGPY—CO medium to which 0.1% cholesterol was added (hereinafter abbreviated to SGPY—CO—CS medium). The results are shown in Table 1.

The average multiplication number is an average of multiplication numbers of kushidai cultivated in five vessels under the same conditions.

TABLE 1

| medium | average multiplication number |
|---|---|
| SGPY | 0 |
| SGPY-CO | 410000 |
| SGPY-RO | 240000 |
| SGPY-LO | 560000 |
| SGPY-SO | 0 |
| SGPY-OO | 38700 |
| SGPY-CS | 288000 |
| SGPY-CO-CS | 470000 |

It has been found from the results that kushidai multiplies under varied conditions though kushidai does not multiply in SGPY medium or SGPY—SO medium. A comparison in multiplication number among SGPY medium, SGPY—CO medium, SGPY—CS medium and SGPY—CO—CS medium shows that, while vegetable oils promote multiplication rate, cholesterol helps in multiplication of kushidai but further promotes multiplication rate in media to which vegetable oils are added.

A microscopic observation of kushidai having multiplied in SGPY—CO—CS medium shows that most have grown to infective juveniles of the next generation, without variations in the degree of growth. On the other hand, a similar observation of kushidai having multiplied in SGPY—CO medium again has shown no variation in the degree of growth. From these results, it is seen that kushidai grows regardless of presence or absence of cholesterol, and that cholesterol imparts no influence on morphological growth of kushidai.

(2) A bioassay was carried out by the soil mixing method using 1000 kushidai multiplied in each of the above-mentioned SGPY—CO medium, SGPY—RO medium, SGPY—LO medium, SGPY—OO medium, SGPY—CS medium and SGPY—CO—CS medium, and larvae in the third instar of Anomala cuprea Hope as sample insects. The results are shown in Table 2.

In Table 2, the insecticidal rate represents percentage of average numbers of death of the sample insects with respect to 10 insects when 10 each of the sample insects were bred at 25° C. for 10 days.

TABLE 2

| medium | insecticidal rate (%) |
|---|---|
| SGPY-CO | 10 |
| SGPY-RO | 10 |
| SGPY-LO | 10 |
| SGPY-OO | 10 |
| SGPY-CS | 90 |
| SGPY-CO-CS | 100 |

It is seen from Table 2 that the kushidai cultivated in the media containing no cholesterol show only low insecticidal activity, but the kushidai cultivated in the media containing cholesterol show a high insecticidal activity. A similar assay was carried out by increasing the kushidai cultivated in SGPY—CO medium to 4000 per larva of Anomala cuprea Hope. However, this showed no improvement in insecticidal activity, and it has also been found that the presence or absence of corn oil has no influence on the insecticidal activity. It may be said that the insecticidal activity of kushidai may be increased in the presence of steroids typified by cholesterol.

(3) The insecticidal activity to kill larvae in the third instar of Anomala cuprea Hope and the dependence on the number of kushidai thereof were checked by applying, per larva, 250 to 1000 kushidai cultivated in SGPY—CO—CS medium. Table 3 shows the results of this bioassay carried out by the soil mixing method as in test 1-(2).

TABLE 3

| number inoculated | insecticidal rate (%) |
|---|---|
| 250 | 30 |
| 500 | 70 |
| 1000 | 100 |

It is seen from these results that the kushidai cultivated in the media containing cholesterol show a high insecticidal activity even if inoculated in small numbers.

Comparative Example: Influence of Cholesterol on Other Nematodes

How cholesterol plays a part in the multiplication characteristic and insecticidal activity of ALL was examined.

(1) The multiplication characteristic was checked of 2000 ALL cultivated in each of SGPY medium, SGPY—CO medium, SGPY—CS medium and SGPY—CO—CS medium. The results are shown in Table 4.

TABLE 4

| medium | average multiplication number |
|---|---|
| SGPY | 0 |
| SGPY-CO | 137000 |
| SGPY-CS | 15700 |
| SGPY-CO-CS | 306000 |

It is seen from the results that, as distinct from Test 1, the addition of corn oil helps in multiplication of ALL, but corn oil alone produces little effect, and that the addition of cholesterol remarkably promotes the multiplication characteristic.

(2) ALL multiplied in each of the above-mentioned SGPY—CO medium and SGPY—CO—CS medium were placed in contact in varied numbers 500, 1000 and 2000 to evaluate their insecticidal activity to kill larvae in the sixth instar of common cutworm, by the paper contact method to derive average time of death from insecticide rates checked every 12 hours. The results are shown in Table 5.

TABLE 5

| medium | no. inoculated | insecticidal rate (%) 12 | 24 | 36 | 48 (hr) | average time of death (hr) |
|---|---|---|---|---|---|---|
| SGPY-CO | 500 | 0 | 20 | 50 | 100 | 39.6 |
|  | 1000 | 10 | 30 | 80 | 100 | 33.6 |
|  | 2000 | 20 | 40 | 100 | — | 27.6 |
| SGPY-CO-CS | 500 | 0 | 10 | 40 | 100 | 42.0 |
|  | 1000 | 20 | 30 | 70 | 100 | 33.6 |
|  | 2000 | 30 | 50 | 100 | — | 26.4 |

It is seen from Table 5 that, in cultivating ALL, whether cholesterol is included in medium or not does not influence the insecticidal activity with respect to larvae of common cutworm.

(3) Tests similar to (1) and (2) were carried out on Steinernema carpocapsae DD-136, which produced results similar to the case of ALL.

Test 1 and the comparative example suggest that cultivation of nematodes parasitic on insects in a medium containing cholesterol increases the insecticidal activity which is peculiar to kushidai, and demonstrate that the kushidai multiplied in this way have a high degree of insecticidal activity.

That is, it has been found that the kushidai multiplied in this way may be used as a biological agrochemical having a high degree of insecticidal activity with respect to larvae of Anomala cuprea Hope and the like.

Test 2: Dependence of Insecticidal Activity on Amount of Cholesterol Added

What amount of cholesterol added may improve the insecticidal activity of kushidai was examined.

After preparing a saturated solution of cholesterol dissolved in ethanol, a predetermined amount of corn oil was added to this saturated solution to make an emulsion. The above-mentioned SGPY medium was added to the emulsion to adjust so that cholesterol content was 1000 mg/l (0.1%) and corn oil content was 3%. By preparing a medium in this way, cholesterol dissolved in ethanol may be dispersed uniformly in the medium, nematodes may be multiplied uniformly in the medium, and they may be multiplied efficiently.

Similarly, cholesterol containing media were prepared with cholesterol contents at 25, 50, 100, 200 and 400 mg/l. 1000 kushidai were cultivated in each of these media at 25° C. and at 70% relative humidity for 20 days, to examine their multiplication characteristics. The multiplied kushidai were used in 1000s to examine the insecticidal activity thereof with respect to larvae of Anomala cuprea Hope by the soil mixing method. The results are shown in Table 6.

TABLE 6

| cholesterol content (mg/l) | average multipl. | insecticidal rate (%) 2 | 4 | 6 | 8 | 10 (days) |
|---|---|---|---|---|---|---|
| 0 | 250000 | 0 | 0 | 0 | 0 | 0 |
| 25 | 196000 | 0 | 0 | 10 | 20 | 40 |
| 50 | 236000 | 0 | 30 | 50 | 80 | 100 |
| 100 | 260000 | 0 | 30 | 70 | 90 | 100 |
| 200 | 247000 | 10 | 50 | 80 | 100 | — |
| 400 | 247000 | 10 | 50 | 80 | 100 | — |
| 1000 | 280000 | 40 | 60 | 90 | 100 | — |

It is seen from Table 6 that cholesterol has little influence on improvement in the multiplication of kushidai. On the other hand, it is seen that the insecticidal activity with respect to Anomala cuprea Hope is promoted with an increase in the amount of cholesterol added.

Further, according to this table, the insecticidal rate becomes 100% in 10 days where cholesterol content is 50 mg/l or more. Thus, a sufficiently high degree of insecticidal activity is achieved with respect to Anomala cuprea Hope.

Test 3: Influence of Steroid Other than Cholesterol on Insecticidal Activity

The multiplication characteristic and insecticidal activity of kushidai were examined with a medium including 4-cholesten-3-one as asteroid other than cholesterol.

Specifically, a medium (SGPY—CO—CSN medium) containing 0.1% 4-cholesten-3-one and 3% corn oil was prepared and 1000 kushidai were cultivated at 25° C. and at 70% relative humidity for 20 days to examine their multiplication characteristics. Further, the multiplied kushidai were used in 1000s to examine the insecticidal activity thereof with respect to larvae of Anomala cuprea Hope by the soil mixing method, by means of insecticidal rate with respect to larvae of Anomala cuprea Hope occurring in 10 days. Besides, for comparison purposes, the multiplication characteristics and insecticidal activity were also examined with SGPY—CO—CS medium and SGPY—CO medium. The results are shown in Table 7.

TABLE 7

| medium | average multipl. number | insecticidal rate (%) |
|---|---|---|
| SGPY-CO-CSN | 408000 | 100 |
| SGPY-CS | 312000 | 100 |
| SGPY-CO-CS | 440000 | 0 |

It is seen from Table 7 that, with use of 4-cholesten-3-one, the insecticidal activity of kushidai may be improved while maintaining the multiplication characteristics at high level.

That is, it has been found that various steroids may be used instead of being limited to cholesterol. The steroids used in the present invention are not limited to cholesterol and 4-cholesten-3-one but include nutrients, such as egg yolk, animal liver oil and the like, having high concentrations of cholesterol and the like.

Test 4: Cultivation of Kushidai Using Supports

In all of the foregoing tests, cultivation were carried out in form of ordinary agar media. On the other hand, a medium was adsorbed to supports, and cultivation was carried out in a layer of the supports, to examine multiplication characteristics and insecticidal activity. This will be described hereinafter with reference to a drawing.

As shown in FIG. 1, a container 1 of 370 mm (W) X 510 mm (L) X 120 mm (H) and having vent holes 1a in upper positions thereof contained a plurality of 3 cm square polyurethane foam cubes to act as supports 2. The plurality of supports 2 were stacked with gaps thereamong, and 3000 ml of the above-mentioned SGPY—CO—CS medium 3 was adsorbed and supported by the supports 2 to form a layer.

After a usual sterilization process for the layer, 500,000 kushidai were inoculated into the layer, and cultivated at 25° C. and at 70 relative humidity for 20 days, to examine their multiplication characteristics. The multiplied kushidai were used in 1000s to examine the insecticidal activity thereof with respect to larvae of Anomala cuprea Hope by the soft mixing method, by means of insecticidal rate with respect to larvae of Anomala cuprea Hope occurring in 10 days.

As a result, the multiplied kushidai reached 105,000,000 to indicate a multiplication rate of at least 200-fold. The insecticidal rate was 100%, and thus a high insecticidal rate was achieved.

Thus, it has been found that multiplication using said layer, while effectively utilizing space, provides kushidai having a high multiplication rate and high insecticidal activity.

Test 5: Study of Multiplication Characteristics by Liquid Medium

In Test 4, cultivation was carried out with a solid layer medium. Whether a high multiplication characteristic and insecticidal activity can be obtained with a liquid medium was also checked.

Specifically, SGPY liquid medium was prepared by adding cholesterol dissolved in heated corn oil to an aqueous solution of 0.6% soluble starch, 1.0% D-glucose, 1.5% bactopeptone and 1.5% yeast extract, whereby the mixture included 0.1% cholesterol and 3% corn oil. Kushidai was cultivated using this SGPY liquid medium in a cultivating tank. This will be described hereinafter with reference to a drawing.

Figure 2:
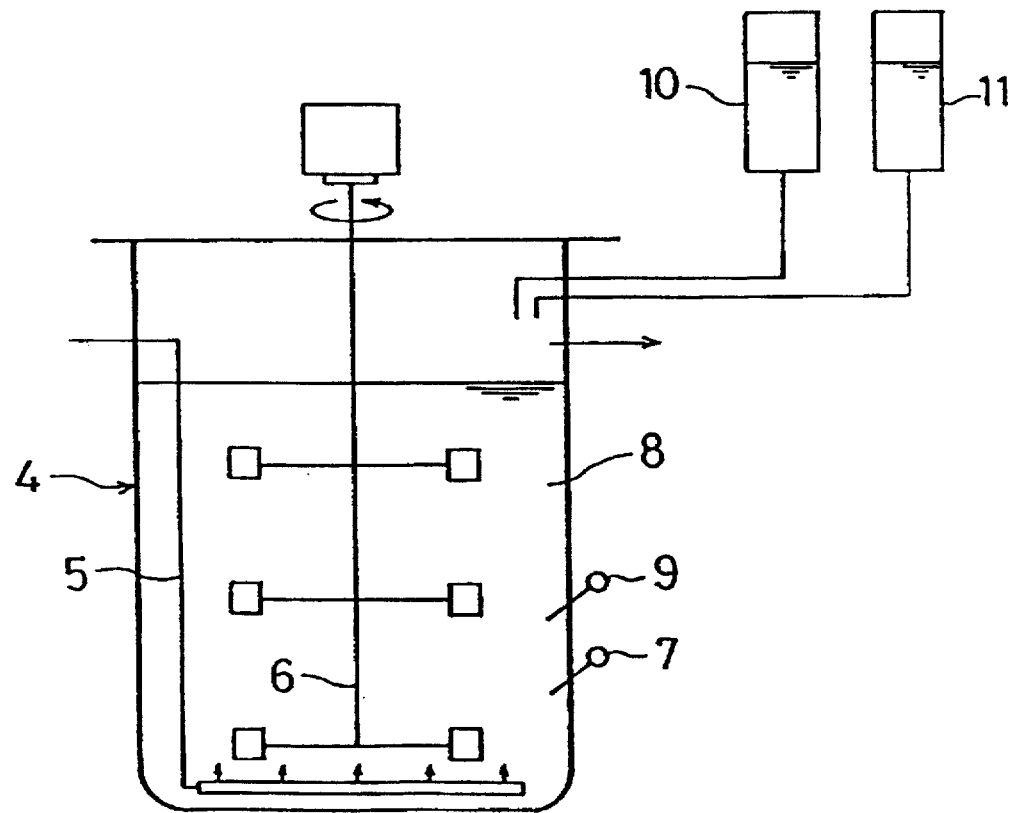
FIG. 2 is a schematic view showing a cultivating method in Test 5.

As shown in FIG. 2, a cultivating tank 4 has therein a sparger 5 for supplying air and agitating blades 6 for dissolving oxygen. A fixed quantity of air can be supplied through the sparger 5. A rotating rate of the agitating blades 6 is controllable based on an excess/shortage of dissolved oxygen in SGPY liquid medium 8 detected by a dissolved oxygen concentration meter 7 extending from inside the cultivating tank 4. Further, pH value of SGPY liquid medium 8 is detected by a pH meter 9 extending from inside the cultivating tank 4. Thus, pH value of medium 8 is controllable to be in an appropriate range (pH 6.5 to 7.5) by adding acid or alkali from acid and alkali chemical pots 10, 11 as necessary.

250 kushidai were inoculated per ml of SGPY liquid medium and cultivated in said cultivating tank 4 at 25° C. for 20 days. Their multiplication characteristics were checked while supplying sufficient oxygen to the kushidai. The multiplied kushidai were used in 1000s to examine the insecticidal activity thereof with respect to larvae of Anomala cuprea Hope by the soil mixing method, by means of insecticidal rate with respect to larvae of Anomala cuprea Hope occurring in 10 days.

As a result, the multiplied kushidai reached 100,000 per ml of the medium to indicate a multiplication rate of at least 400-fold. The insecticidal rate was 100%, and thus a high insecticidal rate was achieved.

It follows that media used in the Nematoda multiplying method of the present invention may be not only solid media but liquid media. The cultivating container 4 is not limited to the cultivating tank having the sparger and agitating blades 6. A flask may simply be used to allow shaking and agitation, to cause liquid medium to contact air by shaking or agitation for oxygen supply. A known technique may be used in place of the method of this embodiment as means for supplying oxygen to liquid medium 8.

Other Embodiments

The foregoing embodiment exemplifies use of kushidai to kill larvae of Anomala cuprea Hope by way of experiment. The invention may be worked as follows.

A biological agrochemical was prepared to contain 100,000/ml of kushidai cultivated in the above-mentioned SGPY—CO—CS medium, and was distributed in soil of a field to have 330,000 kushidai/m2. Sweet potato was planted in the field, and an extent of plague caused by harmful insects was checked at sweet potato harvest.

As a result, it has been found that the extent of plague was significantly reduced compared with an ordinary agrochemical (Fenthion Granule of Nippon Bayer Agrochem Co.) used in an ordinary way (to distribute in a field in a quantity of 9 kg/10 a at planting time, and to distribute in the field three times in a quantity of 9 kg/10 a during a growing period).

The media such as SGPY medium used in the above embodiments and tests, harmful insects typified by larvae in the third instar of Anomala cuprea Hope, and crops typified by sweet potato, are examples illustrating modes of implementation. The present invention is not limited to these embodiments or test modes.

While the claim include reference numerals for expediency of comparison to the drawings, such inclusion does not limit the present invention to the constructions in the accompanying drawings.

We claim:

1. A method of increasing insecticidal activity of *Steinernema kushidai* comprising culturing *Steinernema kushidai* in a culture medium containing a steroid in an amount sufficient to increase insecticidal activity of said *Steinernema kushidai*.

2. The method of claim 1 wherein the steroid is dissolved in heated oil prior to being added to the culture medium.

3. The method of claim 1 comprising dissolving the steroid in an organic solvent, adding heated oil to the solvent, preparing an emulsified suspension from the steroid dissolved in the solvent and the heated oil and adding the suspension to the culture medium.

4. The method of claim 1 wherein the steroid is selected the group consisting of cholesterol and 4-cholesten-3-one.

5. The method of claim 4 wherein the cholesterol is at a quantity of at least 50 mg/l.

6. The method of claim 1 wherein the culture medium comprises 3% corn oil, 0.1% cholesterol and SGPY medium which is prepared by adjusting an aqueous solution of 0.6% soluble starch, 1.0% D-glucose, 1.5% bactopeptone, and 1.5% yeast extract to a pH of about 7.0 with sodium hydroxide, and adding 0.3% agar.

7. A method of increasing insecticidal activity of *Steinernema kushidai* comprising adsorbing culture medium containing a steroid in an amount sufficient to increase insecticidal activity of said *Steinernema kushidai* in at least one solid support and culturing *Steinernema kushidai* on said at least one solid support.

8. The method of claim 7 comprising dissolving the steroid in heated oil prior to adding the steroid to the culture medium.

9. The method of claim 7 comprising dissolving the steroid in an organic solvent, adding heated oil to the solvent, preparing an emulsified suspension from the steroid dissolved in the solvent and adding the suspension to the culture medium.

10. The method of claim 7 wherein the steroid is selected from the group consisting of cholesterol and 4-cholesten-3-one.

11. The method of claim 10 wherein the cholesterol is at a quantity of at least 50 mg/l.

12. The method of claim 7 wherein the culture medium comprises 3% corn oil, 0.1% cholesterol and SGPY medium which is prepared by adjusting an aqueous solution of 0.6% soluble starch, 1.0% D-glucose, 1.5% bactopeptone, and 1.5% yeast extract to a pH of about 7.0 with sodium hydroxide, and adding 0.3% agar.

* * * * *

UNITED STATES PATENT AND TRADEMARK OFFICE
CERTIFICATE OF CORRECTION

PATENT NO. : 5,694,883
DATED : December 9, 1997
INVENTOR(S) : Tachibana et al.

It is certified that error appears in the above-identified patent and that said Letters Patent is hereby corrected as shown below:

On the title page item [57], Abstract, on lines 9, 12, and 15, "asteroid" should be -- a steroid --.

In column 1, lines 36, 44, 50, 52, 53, and 60; column 2, lines 7, 10, and 13; and column 6, line 36, change "asteroid" to -- a steroid --.

In Claim 4, column 8, line 56, after "selected" add -- from --.

Signed and Sealed this

Fourth Day of January, 2000

Attest:

Attesting Officer

*Acting Commissioner of Patents and Trademarks*